United States Patent
Puddu et al.

(10) Patent No.: US 12,344,885 B2
(45) Date of Patent: Jul. 1, 2025

(54) MARKED ITEMS AND VERIFICATION METHODS

(71) Applicant: Haelixa AG, Kemptthal (CH)

(72) Inventors: Michela Puddu, Zürich (CH); Gediminas Mikutis, Zürich (CH)

(73) Assignee: Haelixa AG, Kemptthal (CH)

( * ) Notice: Subject to any disclaimer, the term of this patent is extended or adjusted under 35 U.S.C. 154(b) by 1172 days.

(21) Appl. No.: 17/259,592

(22) PCT Filed: Jul. 9, 2019

(86) PCT No.: PCT/EP2019/068452
§ 371 (c)(1),
(2) Date: Jan. 12, 2021

(87) PCT Pub. No.: WO2020/011807
PCT Pub. Date: Jan. 16, 2020

(65) Prior Publication Data
US 2021/0332426 A1  Oct. 28, 2021

(30) Foreign Application Priority Data

Jul. 13, 2018 (EP) .................................. 18183498

(51) Int. Cl.
*C12Q 1/68* (2018.01)
*C12Q 1/6806* (2018.01)
(Continued)

(52) U.S. Cl.
CPC ... *C12Q 1/6806* (2013.01); *B01J 2219/00572* (2013.01); *B01J 2219/00596* (2013.01);
(Continued)

(58) Field of Classification Search
None
See application file for complete search history.

(56) References Cited

U.S. PATENT DOCUMENTS

| 4,767,205 A | 8/1988 | Schwartz et al. |
| 5,688,642 A | 11/1997 | Chrisey et al. |

(Continued)

FOREIGN PATENT DOCUMENTS

| CN | 107 699 609 | 2/2018 |
| CN | 107 916 263 | 4/2018 |

(Continued)

OTHER PUBLICATIONS

Daniela Paunescu et al: "Detecting and Number Counting of Single Engineered Nanoparticles by Digital Particle Polymerase Chain Reaction", ACS Nano, vol. 9, No. 10, Oct. 27, 2015 (Oct. 27, 2015), pp. 9564-9572.

(Continued)

Primary Examiner — Stephanie K Mummert
(74) Attorney, Agent, or Firm — Renner, Otto, Boisselle & Sklar, LLP

(57) ABSTRACT

The invention provides methods for stably immobilizing nucleic acid tracers onto surfaces of products and objects. This method is applied for the identification and authentication of the marked object or product. The present invention further provides specific coated articles and their use in product verification; processes for manufacturing such coated articles, methods for the verification of the coated article, methods for the quantification of the coated article blending, and products suitable for such verification and quantification method.

8 Claims, 2 Drawing Sheets

(51) Int. Cl.
  *B01L 3/00* (2006.01)
  *B42D 25/36* (2014.01)
  *G07D 7/14* (2006.01)
(52) U.S. Cl.
  CPC ............... *B01J 2219/00605* (2013.01); *B01J 2219/00722* (2013.01); *B01L 3/54* (2013.01); *B42D 25/36* (2014.10); *C03B 2215/404* (2013.01); *G07D 7/14* (2013.01)

(56) References Cited

U.S. PATENT DOCUMENTS

| | | | |
|---|---|---|---|
| 6,048,695 | A | 4/2000 | Bradley et al. |
| 8,329,299 | B2 | 12/2012 | Seal et al. |
| 9,850,531 | B2 | 12/2017 | Grass et al. |
| 9,919,512 | B2 * | 3/2018 | Jung ................. G07D 7/14 |
| 2005/0214532 | A1 * | 9/2005 | Kosak ................. C12Q 1/6813 428/364 |
| 2012/0277108 | A1 | 11/2012 | Minjoung et al. |
| 2012/0283379 | A1 | 11/2012 | Auger et al. |
| 2019/0365063 | A1 | 12/2019 | Nyfeler et al. |

FOREIGN PATENT DOCUMENTS

| | | | |
|---|---|---|---|
| EP | 2 644 703 | 10/2013 | |
| EP | 2644703 A1 * | 10/2013 | ............... B01L 3/54 |

OTHER PUBLICATIONS

Daniela Paunescu et al: "Protection and Deprotection of DNA-High-Temperature Stability of Nucleic Acid Barcodes for Polymer Labeling", Angewandte Chemie, International Edition, vol. 52, No. 15, Apr. 8, 2013 (Apr. 8, 2013), pp. 4269-4272.

European Patent Office, International Search Report and Written Opinion of the International Searching Authority for PCT/EP2019/068452, Oct. 17, 2019.

* cited by examiner

MARKED ITEMS AND VERIFICATION METHODS

This application is a national phase of International Application No. PCT/EP2019/068452 filed Jul. 9, 2019 and published in the English language, which claims priority to European Application No. EP 18183498.7 filed Jul. 13, 2018, both of which are hereby incorporated herein by reference.

The present invention relates to methods for achieving stable immobilization of nucleic acid tracers onto surfaces of items and subsequently detecting the nucleic acid to verify said item. Accordingly, the present invention provides in one aspect items comprising a specific coating; this coating allows to verify the item. As described herein, nucleic acid tracers are stably immobilized onto surfaces of items within said coating. The invention relates in a further aspect to methods for identification of said item. The invention also relates to new uses of specific coatings and to methods of manufacturing coated items.

Counterfeiting and blending of high-valued material/items with cheaper material/items is a known problem. Tracing back the origin of materials/items in complex supply chains is a further recognized problem. Various markers have been proposed as strategies against counterfeiting and improving supply chain transparency. Marking technologies include the use of magnetic inks, photoluminescent/ultraviolet inks, isotopes, polypeptides and nucleic acids.

A drawback of current marking technologies is the limited number of distinct codes available, and the cost and complexity of detection. A further drawback of current tracers is that they are easy to remove if they are not embedded within the item/material. However, embedding is not an option for certain items, where markers can be applied only superficially (e.g. hard raw materials such as beans, or finished products). Superficially, loosely applied marker's durability is limited as markers can be easily removed by chemical or mechanical means (e.g. chemical and solvent washing, ultrasonic cleaning, abrasive cleaning methods). All these drawbacks add a significant amount of costs and risks to marking-related activities.

It is known to use microbeads as tracers. Swartz et al (U.S. Pat. No. 4,767,205) describe a composition and a method for hidden identification. The method uses microbeads of precise size, shape and colour which are transferred to an item to be verified. Although suitable, the method suffers in practice from various drawbacks. Particularly, a reliable analysis is time-consuming and features poor portability, requires a high particle concentration. Further, the limited number of microbeads available only allows for a limited number of codes, thus the method is only an option for verification of a small number of articles.

It is known to use nucleic acids as tracers. DNA offers unique opportunities as a tracer, as a theoretically unlimited number of unique sequences (codes, tags, fingerprints) can be provided, and mature, simple, on-site DNA analytic procedures are available. In particular, quantitative polymerase chain reaction (qPCR) is a widespread method to detect and quantify minute amounts of DNA. Portable qPCR devices are commercially available to perform spot checks. For example, Paunescu et al (ACS nano 2015, 9 (10), 9564-9572) provides a quantification technique for measuring ultralow concentrations of DNA-comprising particles in drinking water. Therefore, several attempts to use DNA as product marker have been made. Grass et al (EP2644703) describe molecular code systems, useful to verify articles. Although suitable, the method suffers in practice from some drawbacks. Particularly, it may happen that the marked items show false negative results, i.e. a genuine item is incorrectly identified as false item. It is apparent that such false analysis has significant impact to the user and should be avoided. Furthermore, Grass et al do not describe how to quantify the tracer. Consequently, Grass et al do not disclose how to detect blending of an item with cheaper/fake copies. Similarly, Zhang et al (CN107699609) discloses a method for preparing genetic tracer and anti-counterfeit nanoparticles based on DNA and nanoparticles. The nanoparticles used are of the core-shell type. The method suffers from the same drawbacks as above: particularly, it may happen that the marked items show false negative results and reliable quantification is not possible.

Therefore, there is a need for methods of marking an item, overcoming one or more of the shortcomings of the prior art. In consequence, there is a need for alternative, particularly durable methods to verify an item. The present invention particularly aims to provide durable, stable and detectable marking of an item, for the purposes of identification, authentication, tracking and tracing of a large number of individual items.

The present invention will be described in more detail below. Unless otherwise stated, the following definitions shall apply in this specification:

It is understood that the various embodiments, preferences and ranges as provided/disclosed in this specification may be combined at will. For example, specific embodiments of the coating (e.g. its coverage) may be combined with specific embodiments of the tracer (e.g. its encapsulation) and combined with specific items (e.g. its type or its surface characteristics).

Further, depending of the specific embodiment, selected definitions, embodiments or ranges may not apply. As used herein, the term "a", "an", "the" and similar terms used in the context of the present invention (especially in the context of the claims) are to be construed to cover both the singular and plural unless otherwise indicated herein or clearly contradicted by the context. The term "containing" shall include "comprising", "essentially consisting of" and "consisting of".

The term "nucleic acid" is known in the field and includes both, naturally occurring nucleic acids and artificial nucleic acids ("analogues"), both single-stranded and double-stranded.

The term "silica" is known in the field and describes the chemical compound $SiO_2$ in its amorphous state. The term "silica" also includes amorphous glass matrices. Suitable glass matrices have a $SiO_2$ content of at least 50 wt %. Glass matrices consequently may include other elements (particularly selected from the group consisting of carbon, hydrogen, nitrogen, sodium, calcium, cadmium, boron, lead, phosphorous, titanium, zinc, cerium, iron, cobalt, and aluminum).

The term "coating" is used in the generic sense to include any covering that is applied to the surface of an object, usually referred to as the substrate. The coating may be completely covering the substrate, or it may only cover parts of the substrate.

The term "tracer" as used herein denotes a marker substance, optionally in combination with other marker substances. The marker or combination thereof are affixed to an item to identify it, or to identify its origin or to verify the properties of the item, or to authenticate the item, or to exclude counterfeit items, or to quantify the blending extent of an item.

The tracer can be, for example, specific to the manufacturer or retailer, or to the particular lot or batch of the item, or to the date of manufacture, or specific to the actual article model or version.

The term "item" is used in its broadest sense and denotes any solid item, such as an article (e.g. luxury goods, cash, valuables, clothing), a device (e.g. automotive parts, electronic devices), bulk material (e.g. paper, fiber, fabric, wood, plastic, mineral), consumer goods (e.g. cosmetics, personal care products, food/pharmaceuticals). The term thereby includes raw materials and finished products. The term further includes commodities and differentiated products.

The term "particle" describes solid spheres with a primary diameter between 10 and 10000 nm, preferably 100 and 1000 nm. The term "particle" also includes larger particles which are composed of aggregates of primary particles with diameters between 10 and 10000 nm. The particle size may be determined by measuring the specific surface areas {e.g. by the BET method).

The term "identification method" covers "verification methods" (i.e. qualitative methods) and "quantification methods" (i.e. quantitative methods). Thus, identification methods allow authentication, tracking and/or tracing of a marked item, and quantifying of blended items.

The term "verification method" describes a method that allows distinguishing and/or identifying articles. Thus, verification methods are suitable (i) for distinguishing authentic products from false articles, (ii) for identification of products (e.g. by batch type, manufacturing site, manufacturing time).

The term "quantification method" describes a method that allows detecting the blending of genuine, high-value and high-quality articles with fake, cheaper and lower quality ones, and determining the extent of such blending.

The present invention will be better understood by reference to the figures.

LIST OF ABBREVIATIONS (1) marked item, and (1') non-marked item
(2) coating
(3) tracer, with (31) ... (34) specific embodiments thereof
(4) matrix
(5) solution of molecular precursor
(6) buffered fluoride solution
(7) catalyst solution
(11) items surface
(a) ... (d) process steps for manufacturing a marked item as described herein
(e) ... (h) process steps for identifying a marked item as described herein
(I), (II), (III) chemical formulae of molecular precursor FIG. 1 schematically illustrates a method of manufacturing a marked item, as further detailed in the first aspect of this invention.

(e1) and (e2) denote the step of providing a marked item and providing a buffered fluoride solution.

(f) denotes the step of contacting said marked item with said buffered fluoride solution, thereby removing at least a part of said coating.

(g1) denotes the step of analysing the thus obtained composition for nucleic acid sequence; (g2) denotes the step of comparing and matching the obtained nucleic acid sequence to a database containing information on nucleic acid sequence in the original item.

(h1) denotes the step of verifying the items authenticity and/or history.

(h2) denotes the step of comparing the concentration of nucleic acid to the concentration in the original item and (including the step of quantifying the items blending extend.

Figure 4:
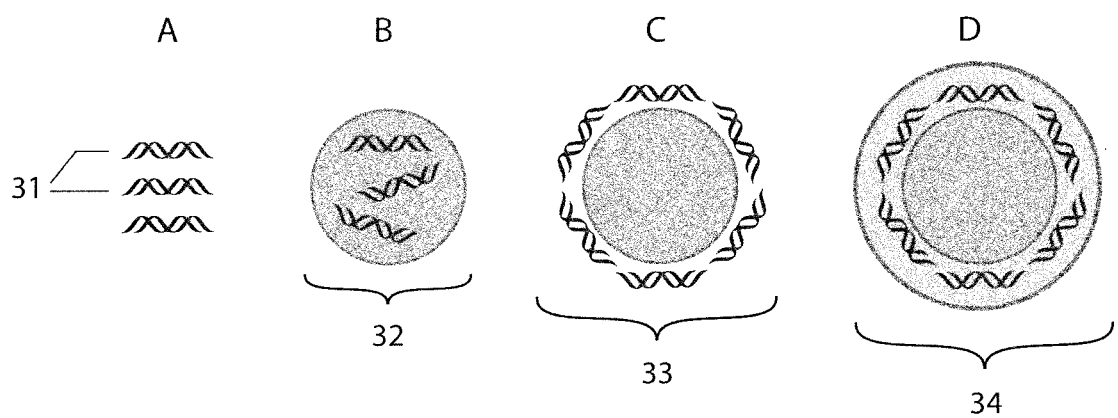

FIG. 4 shows four possible tracer designs according to this invention:
a) tracer consists of free nucleic acids (31);
b) tracer contains nucleic acids encapsulated within particles (32);
c) tracer contains nucleic acids attached to the surface of particles (33);
d) tracer contains nucleic acids attached to the surface of particles, said particles being encapsulated (34).

In general terms, the identification method according to the present invention addresses the issues set forth above. In meeting the stated requirements, the present invention is based upon the use of nucleic acids tracers (3) for identification of an item (1). The tracers are immobilised in a durable way onto surfaces (11) of items (1) via growing a silica coating (2) from suitable precursors. The thus obtained nucleic acid-marked surfaces (11) are then used to verify such items. Accordingly, the overall process of identification includes:

1. Marking of an item by nucleic acid tracer immobilisation, involving the steps of (hereinafter: steps a-d):
   exposing the surface to the nucleic acid tracers (3),
   immobilising the nucleic acid tracers by growing a silica coating (particularly by polycondensation reactions of a molecular precursor-containing solution (5)), and optionally cleaning the thus obtained item (1).

2. Distributing, using the thus marked item (1).

3. Identifying the marked items via nucleic acid tracer read-out (and thereby identifying non-marked items, involving the steps of (hereinafter: steps e-h):
   dissolving the silica coating in fluoride solution (particularly a buffered fluoride solution (6)),
   optionally purifying the thus obtained nucleic acid, and analysing the thus obtained nucleic acid.

The result of the nucleic acid tracer immobilisation is a marked item (1) comprising the original item (1') and an additional coating (2). This item (1) retains the properties of the original, non-marked/non-coated item (1'), and can at any point be subjected to identification.

In line with the above, the marking of an item/method of manufacturing a marked item is described first. In a second aspect, the marked items obtainable by such method are described. In a third aspect, corresponding identification methods are described. In a forth aspect, uses of silica coatings and marking kits are described.

In a first aspect, the invention relates to methods for manufacturing marked items, as described herein. This aspect of the invention shall be explained in further detail below.

Figure 1:
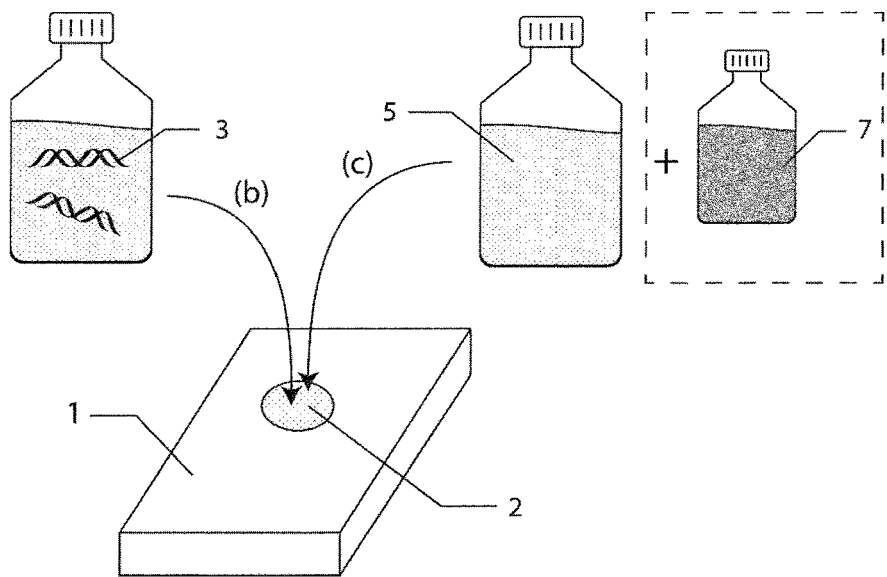
Figure 2:
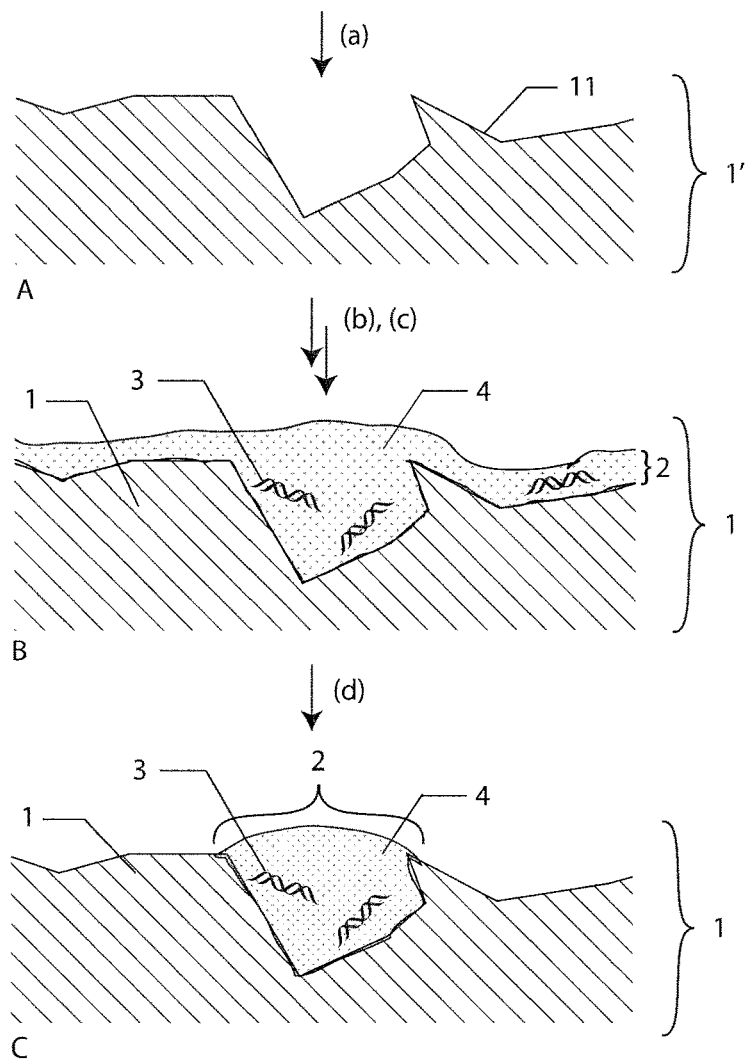
FIG. 2 shows the method of manufacturing a marked item on a microscale, where the tracer and a coating are applied on the surface (11) of the item (1'), and after cleaning the surface (mechanically or chemically), the flat surface-bound coating is removed, but the coating in surface imperfections stays. Accordingly, FIG. 2 also depicts a marked item according to this invention.

The inventive method for marking an item (1') comprises the steps of (a) providing an item (1'), one or more tracers (3), a molecular precursor-containing solution (5) and optionally a catalyst solution (7); and (b) exposing the surface of said item (1') to said one or more tracers; and (c)

subsequently coating said item with said molecular precursor solution (5), and, optionally, said catalyst solution (7), to thereby obtain said marked item (1). The manufacturing may optionally be followed by a cleaning step (d). This manufacturing method is illustrated in FIGS. 1 and 2.

Step (a): The starting materials (1'), (3), (5), and (7) (if present) are provided in a conventional way. They are known per se or obtainable according to known methods. Tracers (3): Suitable tracers are described below, $2^{nd}$ aspect of the invention. Preferably, said one or more tracers (3) are selected from DNA with a length between 50 and 200 nucleotides.

Molecular precursor solution (5): Suitable solutions are described below, $2^{nd}$ aspect of the invention. Preferably said molecular precursor solutions comprise either metal alkoxides of formula (I), functional silanes of formula (II) or polymeric silanes of formula (III), each as described below, $2^{nd}$ aspect of the invention.

Catalyst solution (7): The catalyst solution is optional. Suitable solutions are described below, $2^{nd}$ aspect of the invention. Preferably said catalyst solution is either an acid or a base.

Step (b): Said exposing step (b) may be any conventional step known in the art and includes spraying, immersing the item, or varnishing. Suitable process steps may be selected by the skilled person, depending on the item (1') to be marked and the tracer used.

In one embodiment of step (b), the nucleic acid tracer solution or encapsulated nucleic acid particle suspension is contacted to the surface to mark the item. Suitable processes are selected from spraying, spin-coating and dip-coating. Contacting the surface to the nucleic tracers occurs typically over a period of time between 1 s and 4 h.

Step (c): Said coating step (c) may be any conventional step known in the art and includes spraying, immersing the article, or varnishing. Suitable process steps may be selected by the skilled person, depending on the item (1') to be marked and the matrix used.

In one embodiment of step of step (c), applying the molecular precursor-containing solution (5), and, optionally, the catalyst solution (7), occurs by a process selected from spraying, spin- and dip-coating techniques. The molecular precursor-containing solution is typically applied over a period between 1 second and 4 hours, and readily forms a silica coating.

The molecular precursor-containing solution (5) comprises at least one molecular precursor and water or alcohol (e.g. ethanol, isopropanol) or water/alcohol mixture. The molecular precursor can generally be any silicon alkoxide (e.g., tetraethoxysilane, TEOS, or tetramethoxysilane, TMOS) or mixture of silicon alkoxide and metal or semimetal alkoxide leading to the formation of the silica layer through hydrolysis and condensation reactions.

In one embodiment of the invention, the solution is a solution of TEOS in water. In another embodiment, the solution is TEOS in a water-isopropanol mixture. In a third embodiment, the solution is TEOS in isopropanol.

Optionally, a catalyst solution (7) for the hydrolysis and/or condensation reactions that ultimately result in the coating layer can be added. Suitable catalysts are known in the field and include acids, and bases. In one embodiment of the method according to the present invention, the catalyst is ammonia. In another embodiment, the catalyst is acetic acid. In a further embodiment, the catalyst is an amine-functionalized silane.

It is evident that the catalyst solution (7) has to be kept separately from the precursor solution (5) during shipping and storage, as otherwise the precursor would react/degrade, prior to application on the item's surface. Addition of the catalyst solution (7) may take place either before, after, or simultaneously with the molecular precursor-containing solution (5). Which option to choose depends on the specific case, considering the item to be marked, the type of molecular precursor, equipment available for the coating process and other practical considerations. On the other hand, it is less critical whether the catalyst is applied prior, simultaneously or after the precursor is applied to the surface. As a consequence, in one embodiment, step (c) comprises the subsequent steps of (c1) coating with said solution (5) followed by (c2) coating with said solution (7). In an alternative embodiment, said step (c) comprises the step of (c3) pre-mixing solutions (5) and (7) and subsequent coating of said item with the obtained combined solution of molecular precursor and catalyst.

In general, no external heating is needed since ambient temperature is sufficient.

To induce the growth of a silica layer that anchors the nucleic acids, a potential incompatibility of metal or semimetal alkoxide and nucleic acid chemistry (both carrying a negative charge under reaction conditions) has to be solved.

In one embodiment, said incompatibility is solved by the introduction of co-interacting species (e.g. positively charged aminosilanes such as (3-Aminopropyl)-triethoxysilane (APTES), N-trimethoxysilyl-propyl-N,N,N-trimethylammonium chloride (TMAPS) directing the growth of the silica to the surface of the nucleic acid.

In another embodiment, said incompatibility is solved by introduction of polycationic species (e.g. polyethyleneimine (PEI)) in the tracer mixture to form a DNA/polycationic complex.

In another embodiment, said incompatibility is solved by encapsulating the nucleic acids within oxide particles, acting as nuclei for the silica layer growth. Examples of operable composition of the oxide particles include silica, titania, zirconia. Representative dimensions for a typical nucleic acid-encapsulated particle are in the range of 50 nm to 1 μm in diameter, although these dimensions are not critical and might vary substantially.

In one embodiment of the method according to the present invention, the particle has a core/shell structure and the nucleic acid is sandwiched between the core and the shell. In one embodiment, both the core and the shell are made of silica.

The naked or encapsulated nucleic acid tracers are dispersed in water or in an alcohol (e.g. isopropanol, ethanol). In a preferred embodiment, a nucleic acid-encapsulated particle tracer suspension in isopropanol with a particle concentration of between 1 μg/L and 1 g/L is used.

Step (d): Said cleaning step (d) may be any conventional step known in the art and includes washing the item with a solvent (e.g. stream of water and/or water/alcohol mixture), immersing in a solvent (e.g. water and/or water/alcohol mixture), mechanical cleaning and polishing the marked item. During cleaning, non-bound excess tracer is removed.

To immobilise the nucleic acids to the surface of an item, the method takes advantage of surface indentions, such as roughness, porosity, abrasions and other defects, which are always present to some degree. Before growing into a continuous layer, said indentions are filled with the tracer and the coating material.

It is considered an advantage that the coating acts as a seal preventing the tracer from escaping the indention and stably anchoring it to the article. It is considered a further advantage that the silica matrix stabilizes the tracer against thermal and chemical decay, making the tracer more durable and difficult to remove, as shown in Example 6 and Example 8. Using silica as a matrix further allows fast simple nucleic acid analysis, often without the need for a purification step.

It is considered a further advantage that no covalent bond is formed between the tracer and the silica matrix of coating, avoiding the need to chemically modify the tracer.

The method is particularly suited for items free of silicate on its surface. This is considered a major advantage. While methods to stably apply nucleic acids to silicate surfaces via covalent bonding are available, no durable and easy to apply solution is available for non-silicate surfaces.

Because the coating described herein grows within the surface indentions, it is not removed from such spots even after a harsh cleaning or polishing step as long as the imperfections are present. Again, this is considered a major advantage of the present invention.

In a second aspect, the invention relates to an item comprising a specific coating, hereinafter marked item (1). Accordingly, the invention provides a marked item (1) containing a coating (2), said coating comprises one or more tracers (3) embedded in a matrix (4), wherein (i) the tracer (3) comprises nucleic acids; (ii) the tracer (3) is free of covalent bonds to said item (1); (iii) the tracer is free of covalent bonds to said matrix (4); (iv) the matrix (4) is a silica-matrix and the coating (2) is located on the surface (11) of said item (1). This aspect of the invention shall be explained in further detail below.

Marked item (1): The term marked item as used herein denotes any item comprising a surface suited for the application of a coating. The surface to mark/to identify, can be a simple flat substrate or a surface with multiple indentions. In such indentions, the coating is embedded and cannot be removed easily due to the physical shape of the material.

Suitable items thus include, without limitation: luxury goods; fiber or fabrics; items of clothing and accessories; art pieces; industrial components; auto parts; electronic devices; paper; cash or valuables; packaging material; tobacco; explosives and weapons; wood; pharmaceuticals and beauty items; and food and animal feed.

In one advantageous embodiment, items are selected from the group consisting of luxury goods, fiber or fabrics, items of clothing and accessories, paper, cash or valuables, packaging material, pharmaceuticals and beauty items, and food and animal feed;

In one further advantageous embodiment, items are selected from the group consisting of luxury goods, fiber or fabrics, items of clothing and accessories, cash or valuables, beauty items, and food and animal feed.

Particularly suited are soft porous or fibrous materials such as cellulose, cotton, wool. These items can be more deeply impregnated with the nucleic acids, the molecular-precursor solution, and the fluoride buffer.

The term marked item shall not imply that the item is already verified/quantified. It simply denotes the fact that the item comprises tracers embedded in a matrix. Accordingly, the invention provides for items that are coated with tracers embedded in a matrix and thereby marked. Such items are therefore identifiable and/or traceable once the item's nucleic acid comprising tracer has been read out. The invention thus provides for items that are marked and/or identifiable and/or identified and/or traceable. Such a marked item (1) presents the same features as the non-marked item (1'). At any point in time, it may be subjected to a verification and quantification method.

Inventive marked items (1) (containing a coating as described herein) can be distinguished from known items (e.g. containing a tracer attached on the surface but without a coating, such as according to Grass et al) by immersing the items in an ultrasound bath and quantifying the released tracer. The known items will release a larger fraction of the tracer than the inventive items. This is shown in Example 5 and Example 7 and thus confirms the improvements achieved by the present invention. The inventive items will also release the tracer after solution (6) is applied, whereas known items (e.g. items not containing a silica matrix (4), but a covalent bonding) will not release, or release a smaller fraction of the tracer when solution (6) is applied.

It is known that an item's surface may be characterized by its outer surface roughness. Although many items appear to have a smooth surface, they are in fact rough on a microscopic scale. Such items possess a multitude of indentions; the coatings as described herein fill such indentions and thereby allow deposition of tracers (3). Examples of such items include sheets of paper and coffee beans. The coatings as described herein may be applied to both, rough and smooth surfaces. This allows to mark a broad range of items, irrespective of the items surface roughness.

In one further embodiment of the invention, the item's outer surface (11) is of smooth structure. Such surfaces are characterized by an arithmetic mean surface roughness below 0.8 µm, preferably below 0.4 µm.

In one further embodiment of the invention, the item's outer surface (11) is of rough structure (including porous structures and fibrous structures). Such surfaces are characterized by an arithmetic mean surface roughness above 0.8 µm, preferably above 1.6 µm.

It is known that an items surface (11) may be characterized by its surface chemistry, i.e. the presence/absence of functional groups that may interact with the coating, particularly hydroxyl groups. There is no particular limitation as to the surface chemistry.

In one embodiment, the surface (11) bears —OH groups and the condensation reaction of step (c) can occur between hydrolysed alkoxides and hydroxyl groups of the surface, leading to the covalent bonding of alkoxide to the surface. Items that bear —OH groups on its surface are known in the field. Cotton, wool, wood, paper, metal are named by way of example.

In one further embodiment, the surface lacks —OH groups and the silica coating is deposited onto the surface without generating covalent bonding. Items that lack —OH groups on its surface are known in the field. Polymer materials, such as polyolefines, are named by way of example.

In one further embodiment of the invention, the marked item contains a surface that is not a silicate.

In one further embodiment of the invention, the marked item contains a surface that is inert towards aqueous fluoride solutions, particularly inert towards buffered diluted fluoride solutions.

Coating (2): The coating (2) contains (i.e. comprises or consists of) matrix (4) and embedded therein a multitude of tracers (3). Without being bound to theory, it is believed that the specific coating as described herein significantly improves identification of said item (1). Compared to the prior art, a much broader range of items may be marked. Simultaneously, the accuracy of identification is improved, as less false results are observed and quantification is possible.

As described above (first aspect) the matrix (4) grows on the items surface, thereby strongly adhering to this surface. It is believed that the coating, containing matrix and tracers, provides for two important technical effects.

First, it "glues" on the items' surface (11) and thus fixes the tracer (3) to the item (1). This property of the coating described herein is in sharp contrast to previously known approaches, where tracers in the form of nano-particles are simply deposited on the items surface.

Second, the matrix (4) acts as a barrier, preventing the tracers (3) to escape/to be removed. This is achieved by better adherence to the surface: The coating (2) has in fact higher interface to the surface than a spherical ball (as a model for nano-particle tracers). The matrix further acts as a barrier to prevent access to the tracer from the environment. This is achieved by a matrix of a non-porous structure. While matrices of a porous structure, such as sol-gels, allow access to tracers entrapped in such porous matrices, this is not the case in the present invention. Accordingly, the invention provides for marked items as described herein, where the matrix (4) possesses a non-porous structure. Such non-porous structure entraps the tracer and prevents its access from the outside. Such non-porous structure of the matrix may be easily identified, e.g. by showing that biomolecules do not diffuse in said matrix and/or tracers do not diffuse out of said matrix.

Accordingly, the coating (2) is applied to and thereby located on the surface (11) of said item (1).

In one embodiment, the coating covers at least one, preferably one, macroscopic area of said item. The term macroscopic area, defines an area visible to the naked eye, such as 0.5 cm2 or more. This embodiment is visualized in FIG. 2B. In one alternative embodiment, the coating only covers microscopic indentions of said item. This embodiment is visualized in FIG. 2C. In the latter case, a multitude of microscopic areas is present on the articles surface.

The invention thus provides for marked items as described herein, wherein the item's surface (11) is fully coated with said coating (2) (macroscopic area); or partly coated with said coating (2) (macroscopic area); or only coated with said coating (2) within microscopic area (e.g. indentions/cavities) of said surface (11).

The invention thus relates to a marked item as described herein, wherein said coating (2) fully covers the surface (11) of said item (1). The invention further relates to a marked item as described herein, wherein said coating (2) covers at least one, preferably one, macroscopic surface area (12) of said item. The invention further relates to a marked item as described herein, wherein said coating (2) covers a multitude of, preferably more than 100, microscopic surface areas (13). The invention further relates to a marked item as described herein, wherein said coating (2) is located in a multitude of, preferably more than 100, microscopic indentions (14) present in the surface of said item.

The coating thickness may vary over a broad range, typically between 5 nm and 500 μm, preferentially between 20 nm and 10 μm.

Tracer (3): As discussed above, the tracer comprises nucleic acids. Such tracers may be provided in various forms, as outlined in FIG. 4.

In one embodiment, the tracer (3) consists of free nucleic acids (31). This embodiment is exemplified in ex. 6 and FIG. 4A. Free nucleic acids may be supplied with polycationic species (e.g. PEI) as disclosed in the first aspect to facilitate DNA interface with the matrix.

In one further embodiment, the tracer (3) contains or consist of nucleic acids encapsulated within particles (32). This embodiment is shown in FIG. 4B.

In one further embodiment, the tracer (3) contains or consists of nucleic acids attached to the surface of particles (33). This embodiment is exemplified in ex. 8 and shown in FIG. 4S.

In one further embodiment, the tracer (3) contains or consist of nucleic acids attached to the surface of particles which are encapsulated within particles (34). This embodiment is exemplified in the remaining examples and shown in FIG. 4D.

The term nucleic acid is discussed above. A wide range of nucleic acids may be employed. According to this invention, nucleic acids may be selected from the group consisting of natural occurring nucleic acids and synthetic nucleic acids. The nucleic acids may be selected from the group consisting of DNA, RNA, and PNA. Suitable nucleic acid may be selected from natural sequences (whether isolated from natural sources or synthesized) and synthetically produced non-natural sequences. All or a portion of the nucleic acid may comprise an identifiable sequence. The length of a nucleic acid may vary substantially and includes oligonucleotides, polynucleotides. Representative length for a typical identifiable nucleic acid sequence is in the range of 40 to 200 base pairs.

The loading of nucleic acids in the coating may vary over a broad range, typically between 0.01 parts per trillion and 2 wt %, preferably between 0.1 parts per trillion and 1 part per million.

Matrix (4): As described above the matrix (4) grows on the items' surface (11), thereby strongly adhering to this surface. The matrix hosts the tracers (3), thereby sealing the tracer (3), preventing its removal and preventing its degradation. Such sealing property may be achieved by a non-porous structure of said matrix. Contrary to porous sol-gel matrices known from the prior art, non-porous silica matrices do not allow access to the entrapped tracers by contact with fluidic medium (liquids, gases, biomolecules). Thus, the non-porous silica matrix (4) as described herein entraps said tracer (3). The term non-porous is known in the field and discussed below. The term non-porous silica matrix thereby excludes porous sol-gel silica as described in US2012/0277108. As the skilled person is aware of, reaction conditions define whether sol-gel is porous or non-porous.

The term "non-porous" is known in the field, e.g. as discussed in Grass et al (cited above). It is accepted that the term "non-porous", have a context specific meaning. In the context of the present invention, the term particularly describes a specific property of the matrix and thus also of the coating as disclosed herein, namely a minimum pore volume of relevant pores. Pores are considered relevant (i) if they are of the "open" type, i.e. pores are accessible from (or in communication with) the environment; and (ii) if they are of the "meso" size, i.e. approximately 2-50 nm in diameter. Such pores are described in Kaneko, particularly table 1, which is incorporated by reference (J. Membrane Sci. 1994, 96, 59-89). Advantageously, non-porous matrices/coatings show a pore volume of relevant pores (i.e. open pores of meso size) below 0.3 cm$^3$/g, preferably below 0.05 cm$^3$/g. The relevant pore volume may be determined by nitrogen adsorption and utilization of the Barrett-Joyner-Halenda method. The non-porous nature of the matrix/coating described herein prevents diffusion of molecules (e.g. hydroxyl radicals, biomolecules) to the tracer, thereby protecting the tracer and/or preventing the diffusion of tracers out of the matrix/coating, thereby maintaining the information associated with the item. This non-porous property of the matrix may also be assessed by a stability test using Copper salts, H$_2$O$_2$ and sodium ascorbate; matrices with the pores defined herein are stable over a period of more than 30 min.

Further, the matrix (4) is easily dissolved upon contact with solution (6).

As discussed above, the matrix is obtained in situ, i.e. grown on the surface of an item (1') by application of a precursor material of said matrix. Suitable precursors are known in the field and include metal-alkoxides of a formula (I), functional silanes of a formula (II) and polymeric silanes of a formula (III). These precursors are known per se or obtainable according to known methods. Particularly suitable precursors are defined below:

Metal-Alkoxides of a Formula (I)

$$M^{IV}(OR)_4 \quad (I), \text{ wherein}$$

M represents Si, optionally doped with Ti, Zr, Al, and

R represents independently from each other a C$_{1-4}$ alkyl group.

Functional Silanes of a Formula (II)

$$R'Si(OR)_3, \quad (II), \text{ wherein}$$

R represents independently from each other a C$_{1-4}$ alkyl group, and

R" represents a functional organic group selected from C$_{1-4}$ aminoalkyl, C$_{1-4}$ epoxyalkyl, C$_{1-4}$ vinylalkyl, C$_{1-4}$ (meth)acryloxyalkyl, C$_{1-4}$ isocyanoalkyl, C$_{1-4}$ mercaptoalkyl; and C$_{1-20}$ alkyl.

Polymeric Silanes of a Formula (III)

$$R''Si(OR)_3 \quad (III), \text{ wherein}$$

R represents independently from each other a C$_{1-4}$ alkyl group, and

R" represents a polymeric chain selected from PEGs, polyethylenes, polypropylenes, PVCs, polystyrenes; polyurethanes.

It is evident from the above that besides the simple metal or silicon alkoxides that lead to the formation of an inorganic oxidic coating, organo(alkoxy)silanes (e.g. silane PEGs or silanes with polymerizable organic substituents such as (meth)acrylic, aminoalkyl, epoxyalkyl, vinylalkyl, (meth) acryloxyalkyl, isocyanoalkyl, mercaptoalkyl functional groups) can be used to incorporate organic substituents, wherein the hydrolysis and condensation reactions lead to formation of an organic-inorganic hybrid coating.

Figure 3:
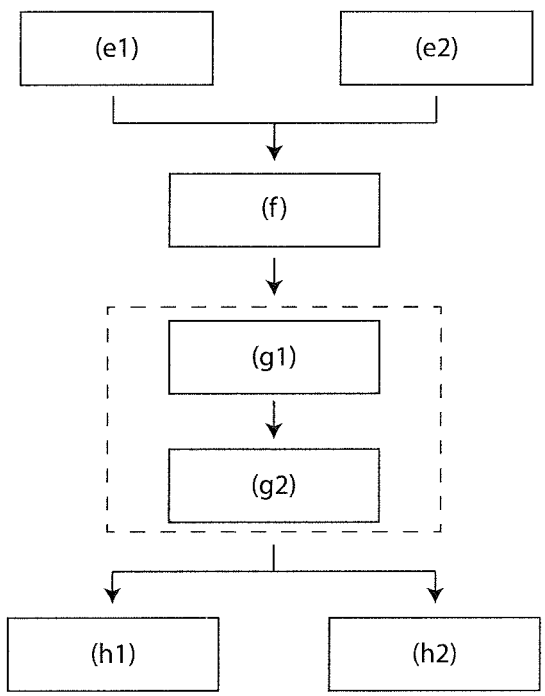
FIG. 3 shows a flowchart for the identification methods of a marked item: verification (left) and quantification (right). Process steps are as follows.

In a third aspect, the invention relates to identification methods for marked items (1), particularly to verification methods and quantification methods. The methods described are suited to distinguish marked (genuine) items from non-marked (false) items. The methods are further suited to identify the marked item and its history, e.g. origin, manufacturer, model, batch etc. They are furthermore suited to quantify the extent of blending of a marked (genuine) item with unmarked (false) item. This aspect of the invention shall be explained in further detail below, also with reference to FIG. 3.

Verification method: In one embodiment a verification method for a marked item as described herein is provided, said method comprising the steps of (e) providing a marked item (1) and a buffered fluoride solution (6); (f) contacting said marked item with said buffered fluoride solution; (g) analysing the thus obtained composition for nucleic acid sequence; (h1) comparing the obtained nucleic acid sequence to the nucleic acid sequence originally introduced into a marked item.

Quantification method: In one embodiment a quantification method for a marked item as described herein is provided, said method comprising the steps of (e) providing the marked item and a buffered fluoride solution (6); (f) contacting said marked item with said buffered fluoride solution, thereby removing part of said coating; (g) analysing the thus obtained composition for nucleic acid sequence; (h2) comparing the concentration of the obtained nucleic acid sequence to the concentration of the nucleic acid sequence originally introduced in the article.

Step (e): In an advantageous embodiment, said aqueous fluoride solution is an aqueous buffered fluoride solution. Preferably, said buffered fluoride solution (6) contains a fluoride salt and hydrofluoric acid.

Step (f): To identify the item, the silica coating is dissolved, which is performed in this step (f). In this step, at least a part of the items coating is removed. The dissolution occurs within seconds. In one embodiment, the item is immersed in the aqueous fluoride solution to dissolve the whole coating. In another embodiment, only a portion of the coating is dissolved, exposing only said portion to the aqueous fluoride solution, e.g. by using a cotton swab or equivalent tool.

Since fluoride buffers dissolve silicates, the method is less suited for products and objects made of said materials such as rocks, porcelain, glasses. Applying fluoride buffers to the surface of said items may result in a damage to the item or negatively influence nucleic acid analysis.

Step (g): In order to purify the nucleic acids obtained, known methods and known reagents/kits may be used, although in many cases purification is not needed. The tracer is identifiable by any suitable nucleic acid analysis method such as polymerase chain reaction and sequencing techniques. The detected nucleic acid sequence is then compared to the one introduced into coating to verify that the article is indeed genuine and/or track back its history. Advantageously, said analysis is selected from qPCR, sequence specific isothermal amplification, and sequencing.

Step (h): Many items are adulterated by dilution of the original product with a low quality, cheaper material ("blended item"). These blends would still be identified as genuine with a verification method (e.g. mixing coated and non-coated cotton would pass the verification method, although the bulk material is not identical to the one to which coating is applied). In order to detect and quantify said dilution of a product, the quantification method allows determining the blending of the coated article with the uncoated one. This is achieved by determining the concentration of the tracer in the coated, potentially blended item using suitable DNA quantification technique (e.g. qPCR). The obtained concentration (c_final) is compared to the concentration in the original marked item (c_original). The fraction of marked item in the blended product corresponds to c_final/c_original×100%, and is a measure of the extent of product dilution.

In a forth aspect, the invention relates to a new uses of silica coatings and to marking kits. This aspect of the invention shall be explained in further detail below.

In one embodiment, the invention relates to the use of a silica coating for immobilizing nucleic acids on an item's surface, characterized in that no chemical bonds between said nucleic acid and said item are formed and no chemical bonds between said nucleic acid and said coating are formed.

The immobilisation of nucleic acid functioning as tracers as described herein is universally applicable to any solid substrates. The method is particularly suited in such cases where the item's solid surface has to resist harsh processing or handling conditions, which could lead to tracer removal, as well as where long term tracer durability is required, to avoid undesired tracer losses. This includes surface treatment of items as claimed.

The immobilised nucleic acids can be used as tracers and can be used in combination with other detectable tracers, such as dyes, wherein the dyes are also incorporated in the coating by dissolving them together with the precursor solution.

Accordingly, the invention relates to the use as described herein (forth aspect) and
said silica coating is as defined in claim 2; and/or
said nucleic acids are as defined in claim 3 or 4; and/or
said silica coating is obtained from a precursor according to formula (I), (II) or (III); and/or
said item is as defined in claim 7 or 8.

In this context, the invention also provides for marking kits. Such kits are suited for coded identification of a selected item (1').

In one embodiment, said kit comprises:
a selected number of containers;
a first group of containers, each comprising a suspension comprising (i) a specific and defined group of nucleic acids as discussed herein; (ii) a precursor for a silica-matrix, as discussed herein; a dispersing medium, particularly an aqueous medium;
optionally a container comprising a solution of a catalyst (7);
optionally a further container comprising buffered fluoride solution (6);
optionally means to apply said solution/suspension contained within said containers to the selected item to be identified.

In one embodiment, said kit comprises:
a selected number of containers; wherein
a first group of containers, each comprising a specific and defined suspension or solution of tracer (3);
a further container comprising a solution of molecular precursor (5);
optionally a further container comprising a solution of a catalyst (7);
optionally a further container comprising a buffered fluoride solution (6); and
optionally means to apply said suspension/solution contained within said containers to the selected item to be identified.

The containers in such kits may be of varying size, depending on the items to be identified. The tracers (3) and precursors (5) may be adapted by the skilled person to the specific needs of the item and the use of such item. Means to apply suspensions/solutions are well-known in the field and include spray nozzles, sponges and the like.

To further illustrate the invention, the following examples are provided. These examples are provided with no intend to limit the scope of the invention.

Example 1: Immobilisation of DNA-Particles on Cotton Surface/TEOS Coating and Further Read-Out Hydrophil cotton sample surface was marked by consecutively spraying the cotton with a 1 g/L DNA-particle suspension in an isopropanol-TEOS mixture (25% v/v), and with an ammonia solution (5 M).

In order to identify the marked cotton, a cotton sample (20 mg) was immersed in 500 µL of a buffered oxide etch solution (0.05 wt fluoride in water). The sample (5 µl) was added to 10 µl of qPCR master mix, 3 µl of ultrapure water, and 2 ul Primer mix (0.5 µM each). qPCR reaction was performed with an Applied Biosystems StepOnePlus system using the following parameters: 95° C. for 10 min, followed by 40 cycles of 15 s at 95° C., and 60 s at 56° C.

The sample required 4.8 cycles to reach a fluorescence threshold value of 0.2; the negative control (ultrapure water, no DNA) required 29.4 cycles, see Table 1.

Example 2: Immobilisation of DNA-Particles on a Diamond Surface/TMOS Coating and Further Read-Out A cut and polished diamond surface was marked by immersing the diamond in 500 µL of a 1 g/L silica-encapsulated DNA-particle suspension (prepared as described in Paunescu, D.; Mora, C. A.; Querci, L.; Heckel, R.; Puddu, M.; Hattendorf, B.; Günther, D.; Grass, R. N. ACS nano 2015, 9 (10), 9564-9572) in isopropanol. The diamond was stirred in the suspension at 900 rpm for 10 min, before adding 40 µL of water and 40 µL of TMOS. The mixture was stirred for another 2.5 h under ambient temperature. The diamond was later extracted from the mixture using tweezers and washed in ethanol.

In order to identify the marked diamond, the item was immersed in 100 µL of a buffered oxide etch solution (0.025 wt % fluoride in water). A sample (5 µl) of the solution containing extracted DNA was added to 10 µl of qPCR master mix, 3 µl of ultrapure water, and 2 ul primer mix (0.05 µM each). qPCR reaction was performed with a Roche LightCycler 96 using these parameters: 95° C. for 10 min plus 40 cycles of 15 s at 95° C. 30 s at 56° C., and 30 s at 72° C., and following the evolution of the fluorescence in real-time.

The earlier the onset of fluorescence (also defined as threshold cycle, when it reaches a relative fluorescence of 0.2), the higher the amount of the specific DNA sequence. Thus, a sample with a threshold cycle of 10 has more of the specific DNA sequence than the sample with a threshold cycle of 11.

The sample extracted from the diamond surface required 15.3 cycles to reach a fluorescence threshold value of 0.2; the negative control (ultrapure water, no DNA) required 29.9 cycles, see Table 1.

Example 3: Immobilization of DNA-Particles on a Metallic Surface/TEOS Coating and Further Read-Out An aluminium surface was marked by immersing the sample in 2 mL of a 1 g/L DNA-particle suspension in an TEOS-isopropanol mixture (15% v/v). The sample was stirred in the suspension at 900 rpm for 15 min, before adding 37.5 µL of water and 37.5 µL of 25% ammonia. The mixture was stirred for another 3 h under ambient temperature. The sample was later extracted from the mixture, washed intensively with ethanol, and further sonicated in ethanol for 5 min using an ultrasonic bath Elmasonic P (37 kHz, 100% power).

In order to identify the marked sample, a cotton swab was wetted in 500 µL of a buffered oxide etch solution (0.05 wt % fluoride in water) and further robbed on a coin area. The swab was then returned into the buffered oxide etch container until analysis. The sample (5 µl) was added to 10 µl of qPCR master mix, 3 µl of ultrapure water, and 2 µl primer mix (0.5 µM each). qPCR reaction was performed with an Applied Biosystems StepOnePlus system using the following parameters: 95° C. for 10 min, followed by 40 cycles of 15 s at 95° C., and 60 s at 56° C.

The sample required 14 cycles to reach a fluorescence threshold value of 0.01; the negative control (ultrapure water, no DNA) required 29.4 cycles, see Table 1.

Example 4: Immobilisation of DNA-Particles on Paper Surface/TEOS Coating and Further Read-Out A paper sample was marked by consecutively spraying the sample with 1 g/L DNA-particle suspension in an isopropanol TEOS mixture (25% v/v) containing PEI (1% wt/v, MW 600, branched), and later with an ammonia solution (5 M). In order to identify each marked paper sample, a cotton swab was wetted in 500 µL of a buffered oxide etch solution (0.05 wt % fluoride in water) and further rubbed on a paper sample area. The swab was then returned into the buffered oxide etch container until analysis. The sample (5 µl) was added to 10 µl of QPCR master mix, 3 µl of ultrapure water, and 2 µl Primer mix (0.5 µM each). QPCR reaction was performed with an Applied Biosystems StepOnePlus system using the following parameters: 95° C. for 10 min, followed by 40 cycles of 15 s at 95° C., and 60 s at 56° C.

The sample required 10.2 cycles to reach a fluorescence threshold value of 0.01; the negative control (ultrapure water, no DNA) required 29.4 cycles, see Table 1.

Example 5: Comparison of the Inventive Immobilization Procedure to the DNA Particle Attachment (Grass et al.)

Two cut and polished diamonds were marked as follows:
1) the first one using the procedure of example 1 (inventive)
2) The second one by immersing and stirring the diamond in 500 µL of a 1 g/L DNA-particle suspension in isopropanol for 2 h.

The two diamonds were later washed intensively with ethanol, and further in ethanol for 20 min using an ultrasonic bath Elmasonic P @37 kHz, 70% power (inventive). In order to identify the marked diamond, the each of the items was immersed in 100 µL of a buffered oxide etch solution (0.025 wt % fluoride in water). Samples of thus obtained solutions (5 µl) were added to 10 µl of qPCR master mix, 3 µl of ultrapure water, and 2 µl primer mix (0.5 µM each). qPCR reaction was performed with a Roche LightCycler 96 using the these parameters: 95° C. for 10 min plus 40 cycles of 15 s at 95° C. 30 s at 56° C., and 30 s at 72° C., and following the evolution of the fluorescence in real-time.

Sample 1 required 22 cycles to reach a fluorescence threshold value of 0.2, while sample 2 required 25.6 cycles. The negative control (ultrapure water, no DNA) required 26.7 cycles, see Table 1.

At a qPCR efficiency of 100%, this means the sample 2 underwent a concentration loss of 92% compared to the immobilized sample (1); thereby clearly showing the importance of a coating.

Example 6: Immobilized Vs Non-Covalently Attached Naked DNA Chemical Stability Test on Leather Two processed leather patches (1×2 cm) were washed with rinsed with water, and then marked as follows:

1) by pipetting 500 µl 0.001 g/L double stranded DNA (61 nucleotides) solution and agitating it for 3 days until it dried out (comparative).
2) By pipetting 500 µl 0.001 g/L double stranded DNA solution followed by adding 1 µl TMAPS, and 1 µL TEOS. The solution was left for 1 h before adding another 10 µl TEOS and 10 µl 25% (v/v) ammonia solution in water, and agitating it for 3 days until it dried out (inventive).

Afterwards both leather items were rinsed with a stream of water and exposed to 1:300 diluted commercial bleach solution (14% activity) for 10 min, followed by heavy rinsing with water.

In order to identify the marked surfaces, 500 µL of a buffered oxide etch solution (0.025 wt % fluoride in water) were added. The sample (5 µl) was added to 10 µl of qPCR master mix, 3 µl of ultrapure water, and 2 µl Primer mix (0.5 µM each). qPCR reaction was performed with a Roche LightCycler 96 using these parameters: 95° C. for 10 min plus 40 cycles of 2 s at 95° C. 12 s at 56° C., and 12 s at 72° C., and following the evolution of the fluorescence in real-time.

Sample 1 did not show any fluorescence (thus, no DNA detected), while sample 2 required 24.1 cycles to reach the fluorescence threshold; the negative control (ultrapure water, no DNA) did not amplify in 40 cycles. This implies that the tracer produced using the comparative method did not survive the harsh chemical treatment, whereas the inventive method resulted in the tracer detection.

Example 7: Immobilized Vs Non-Covalently Attached DNA-Particles on Food

Sample 1 (Grass et al): 10 mf 100 g/L (100 ppm) particle dispersion in ethanol was added to 4 g coffee beans, and the mixture was left shaking for 2 h.

Sample 2 (inventive): 10 mL 100 mg/L (100 ppm) particle dispersion in ethanol was added to 4 g coffee beans, followed by addition of 0.3 mL 25% (v/v) ammonia solution in water, and 0.3 mL TEOS. The mixture was left shaking for 2 h.

The two mixtures were filtered off, and the beans were washed twice with ethanol, and twice with water. The bean dispersions in water were cleaned off by immersing them for 30 s into an ultrasound bath. They were then dried at room temperature overnight. The next day, 4 beans from sample 1 (580 mg) and 4 beans from sample 2 (570 mg) were taken, and 1.5 mL buffered oxide etch solution (0.25% fluoride in water) was added. 30 µL samples were then purified by drop dialysis and analysed by qPCR. Based on the particle calibration curve used during qPCR, sample 1 had 1.7 mg/L DNA tracer concentration (Ct=10.4), and sample 2 had 3.8 mg/L DNA tracer concentration (Ct=9.2), showing that more than twice as many DNA particles survive the ultrasound cleaning when in the silica matrix compared to a known method.

Example 8: Immobilized Vs Non-Covalently Attached Naked DNA Stability Test

This example compares the DNA tracer attachment on the surface by evaporating a DNA solution (comparative, state-of-the-art) on an item to the inventive immobilization.

A polypropylene surface [~1 mm$^2$] was tagged as follows:
1) by pipetting 100 µl 0.001 g/L double stranded DNA (61 nucleotides) solution and leaving it to evaporate overnight. (comparative)

2) By pipetting 250 ul water containing 0.7 mg positively functionalized silica particles (143 nm). In the next step, 10 μg double stranded DNA (61 nucleotides), 0.2 μl TMAPS, and 0.2 μL TEOS were sequentially added. The solution was left for 2 h before adding another 2 μl TEOS, and agitating it for 3 days until it dried out. (inventive)

Afterwards both polypropylene surfaces were rinsed with a stream of water and exposed to 105° C. for 8 h.

In order to identify the marked surfaces, the items were immersed in 2000 μL of a buffered oxide etch solution (0.025 wt % fluoride in water). The sample (5 μl) was added to 10 μl of qPCR master mix, 3 μl of ultrapure water, and 2 μl Primer mix (0.5 μM each). qPCR reaction was performed with a Roche LightCycler 96 using these parameters: 95° C. for 10 min plus 40 cycles of 2 s at 95° C. 12 s at 56° C., and 12 s at 72° C., and following the evolution of the fluorescence in real-time.

Sample 1 did not show any fluorescence (thus, no DNA detected), while sample 2 required 9.2 cycles to reach the fluorescence threshold; the negative control (ultrapure water, no DNA) did not amplify in 40 cycles. Thus, the inventive method allows for thermally stable tagging that is not the case using the free DNA.

TABLE 1

Summary of the DNA concentrations (referred to as Ct values in qPCR). Lower values correspond to higher absolute DNA amounts

| ex. | Sample | Ct value | Ct value neg control |
|---|---|---|---|
| 2 | Diamond + DNA particles + immobilizing layer | 15.3 | 29.9 |
| 5 | Diamond + DNA particles_post sonication | 25.6 | 26.7 |
| 5 | Diamond + DNA particles + immo-bilizing layer_post sonication | 22 | 26.7 |
| 3 | Metal sample + DNA particles + immobilizing layer | 14 | 29.4 |
| 1 | Cotton sample + DNA particles + immobilizing layer | 4.8 | 29.4 |
| 4 | Paper sample + DNA particles + immobilizing layer | 10.2 | 29.4 |
| 6 | Leather + DNA | >40 | >40 |
| 6 | Leather + DNA + immobilizing layer | 24.1 | >40 |
| 7 | Coffee beans + DNA | 10.4 | >40 |
| 7 | Coffee beans + DNA + immobilizing layer | 9.2 | >40 |
| 8 | Polypropylene + DNA | >40 | >40 |
| 8 | Polypropylene + DNA on particles + immobilizing layer | 9.2 | >40 |

Example 9. Quantification of Blending of an Item 4 g coffee beans were coated with a specific DNA sequence as follows:

1) The beans were immersed in 10 mL 100 mg/L DNA particle dispersion
2) 0.3 mL of 25% (v/v) ammonia solution in water and 0.3 mL TEOS were added. The mixture was left shaking for 2 hours.
3) The mixture was filtered off, and the beans were washed twice with ethanol, and twice with water. The bean dispersions in water were cleaned off by immersing them for 30 s into an ultrasound bath. They were then dried overnight at room temperature.
4) 10 beans were weighed out, with different percentage of beans tagged following steps 1-3, and the remaining not tagged original beans, as shown in Table 2.

5) 3 mL buffered oxide etch solution (0.25% fluoride in water) was added. 30 μL samples were then purified by drop dialysis and analysed by qPCR. Based on the particle calibration curve used during qPCR, DNA concentrations were obtained. Detected tagged bean ratio was then calculated as the concentration of the sample divided by the concentration of 10:0 sample.

TABLE 2

Bean blending quantification

| Tagged/non-tagged bean ratio | Mass ratio of tagged beans | Detected tagged bean ratio |
|---|---|---|
| 0:10 | 0.00 | 0.00 ± 0.00 |
| 2:8 | 0.23 | 0.20 ± 0.02 |
| 4:6 | 0.44 | 0.46 ± 0.04 |
| 6:4 | 0.54 | 0.51 ± 0.05 |
| 8:2 | 0.75 | 0.79 ± 0.07 |
| 10:0 | 1.00 | 1.00 ± 0.07 |

The invention claimed is:

1. A marked item containing a coating, said coating comprises tracers in a matrix, wherein:
    the coating is located on, or applied to, a surface of said item; and
    the coating fully covers the surface of said item, or covers at least one macroscopic surface area of said item, or covers a multitude of microscopic surface areas of said item; and
    the coating comprises a multitude of said tracers embedded in said matrix;
    the tracer consists of nucleic acids encapsulated within particles or consists of nucleic acids attached to the surface of particles which are encapsulated within particles; and
    the tracer is free of covalent bonds to said item; and
    the matrix is a silica-matrix, and
    the matrix possesses a non-porous structure, thereby sealing said tracer.

2. The marked item according to claim 1, wherein said coating is additionally located in a multitude of microscopic indentions present in the surface of said item.

3. The marked item according to claim 1, wherein said tracer contains or consist of nucleic acids attached to the surface of particles which are encapsulated within particles.

4. The marked item according to claim 1, wherein said nucleic acids are selected from the group consisting of natural occurring nucleic acids and synthetic nucleic acids.

5. The marked item according to claim 1, wherein said matrix is obtained from a precursor; said precursor is selected from the group of:
    metal-alkoxides of a formula (I)

$M^{IV}(OR)_4$          (I), wherein

M represents Si, optionally doped with Ti, Zr, Al, and
R represents independently from each other a $C_{1-4}$ alkyl group;
functional silanes of a formula (II)

$R'Si(OR)_3$,          (II), wherein

R represents independently from each other a $C_{1-4}$ alkyl group, and
R' represents a functional organic group selected from $C_{1-4}$ aminoalkyl, $C_{1-4}$ epoxyalkyl, $C_{1-4}$ vinyl-alkyl, $C_{1-4}$ (meth) acryloxyalkyl, $C_{1-4}$ isocyano-alkyl, $C_{1-4}$ mercaptoalkyl and $C_{1-20}$ alkyl; and polymeric silanes of a formula (III)

R"Si(OR)$_3$ (III), wherein

R represents independently from each other a C$_{1-4}$ alkyl group, and

R" represents a polymeric chain selected from PEGs, polyethylenes, polypropylenes, PVCs, polystyrenes; polyurethanes.

6. The marked item according to claim 1, wherein said item contains a surface that is not a silicate; and/or that is inert towards aqueous fluoride solutions.

7. The marked item according to claim 1, said item is selected from the group consisting of
luxury goods;
fiber or fabrics;
items of clothing and accessories;
art pieces;
industrial components;
auto parts;
electronic devices;
paper;
cash or valuables;
packaging material;
tobacco;
explosives and weapons;
wood;
pharmaceuticals and beauty items; and
food and animal feed.

8. The marked item according to claim 1, wherein the surface of the item
is of smooth structure, as characterized by an arithmetic mean surface roughness below 0.8 µm; or
is of rough structure as characterized by an arithmetic mean surface roughness above 0.8 µm.

* * * * *